(12) United States Patent
Carter et al.

(10) Patent No.: US 6,383,226 B1
(45) Date of Patent: May 7, 2002

(54) PROSTHESES HAVING CURVILINEAR COLLARS

(75) Inventors: Dennis R. Carter, Stanford; Jay A. Mandell, Saratoga; Gary S. Beaupré, Sunnyvale; David J. Schurman, Stanford, all of CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 0 days.

(21) Appl. No.: 09/094,230

(22) Filed: Jun. 9, 1998

(51) Int. Cl.$^7$ .................................................. A61F 2/36
(52) U.S. Cl. ..................................................... 623/23.21
(58) Field of Search ............................. 623/18, 19, 22, 623/23, 23.21

(56) References Cited

U.S. PATENT DOCUMENTS

| | | | |
|---|---|---|---|
| 3,512,184 A | * 5/1970 | Grove | 623/23 |
| 3,782,373 A | * 1/1974 | Smythe | 623/23 |
| 3,916,451 A | * 11/1975 | Buechel et al. | 623/23 |
| 4,012,796 A | 3/1977 | Weisman et al. | 3/1.91 |
| 4,488,320 A | 12/1984 | Wilson | 3/15 |
| RE32,488 E | 9/1987 | Gustilo et al. | 623/23 |
| 4,908,036 A | * 3/1990 | Link et al. | 623/23 |
| 4,944,762 A | * 7/1990 | Link et al. | 623/23 |
| 5,116,377 A | 5/1992 | Skripitz et al. | 623/23 |
| 5,163,964 A | 11/1992 | Lazzeri et al. | 623/23 |
| 5,197,990 A | 3/1993 | Lawes et al. | 623/23 |
| 5,314,479 A | 5/1994 | Rockwood, Jr. et al. | 623/19 |
| 5,314,489 A | 5/1994 | Hoffman et al. | 623/22 |
| 5,376,124 A | 12/1994 | Gustke et al. | 623/23 |
| 5,387,244 A | 2/1995 | Breard | 623/23 |
| 5,725,594 A | 3/1998 | McTighe et al. | 623/23 |

FOREIGN PATENT DOCUMENTS

| | | | | |
|---|---|---|---|---|
| CH | 426096 | * | 6/1997 | 623/22 |
| FR | 1047640 | * | 12/1953 | 623/23 |
| FR | 2472374 | * | 7/1981 | 623/23 |
| FR | 2616060 | * | 12/1988 | 623/23 |
| FR | 2651674 | * | 3/1991 | 623/22 |

OTHER PUBLICATIONS

Schurman, David S., et al., "C–2 Conical Collar™ Hip System, Unique Axisymmetrical Design Recreates Physiologic Loading Of The Femur," *Kirschner Orthopaedic Division*, 70 West Aylesbury Road, Timonium, Maryland 21093.

* cited by examiner

*Primary Examiner*—David J. Isabella
(74) *Attorney, Agent, or Firm*—Bret E. Field; Bozicevic, Field & Francis

(57) ABSTRACT

Novel prostheses, particularly femoral prostheses, are provided. The subject devices are characterized by the presence of a curvilinear collar. Also provided are methods of implanting a prosthesis in a manner sufficient to provide for a pressure profile at the collar interface in which the pressure increases from the endosteal to the periosteal surface of the bone.

8 Claims, 2 Drawing Sheets

Plane 1
(medial aspect facing out of the plane of the paper)

Plane 2
(medial aspect to the left)

Flat Collar

Conical Collar cone angle cone angle

Collarless, Tapered

Plane 1
(medial aspect facing out of the plane of the paper)

Plane 2
(medial aspect to the left)

Arcuate Curvilinear Collar

Inverse Arcuate Curvilinear Collar

PROSTHESES HAVING CURVILINEAR COLLARS

TECHNICAL FIELD

The field of this invention is orthopaedics.

BACKGROUND OF THE INVENTION

Since its development in the 1960s, total hip arthroplasty has become an important procedure in the field of orthopaedics, and has been characterized as the "greatest single advance in modem orthopaedic surgery." See Finerman, infra. Currently, approximately 125,000 hip replacements are performed in the United States alone each year, where the total cost of such procedures in the United States has been estimated to exceed $3 billion.

As such a variety of devices have been developed for use in hip replacement procedures. Like the natural hip, a hip replacement device consists of a ball and socket joint. Hip replacement involves the implantation (with or without cement) of a metal component having a ball on the upper (proximal) end into the proximal femur and the implantation of a plastic socket component into the pelvis (acetabulum). Loosening leads to pain and bone destruction resulting in the need for surgical revision. Loosening has been attributed to unnatural and inappropriate stresses that exist at the implant collar/bone interface and that exist within the bone (e.g., within the medial femoral cortex).

In an attempt to improve force and stress transfer between implant and bone, many hip replacement designs utilize a collar on the femoral component. Flat collars, as shown in FIGS. 1A and 1B, are one common design. A conical collar, as shown in FIGS. 2A and 2B, has provided improved results and is also currently employed. Other configurations that have been or are currently marketed include the tapered configuration shown in FIGS. 3A and 3B.

While a variety of different configurations have been developed since total hip arthroplasty was first developed, there continues to be interest in the development of new prostheses that can provide for better short- and/or long-term outcomes.

Relevant Literature

Total hip arthroplasty (as well as devices for use therein) is reviewed in Finerman et al., *Total Hip Arthroplasty Outcomes*, (Churchill Livingston, Inc., 1998).

U.S. Pat. Nos. of interest describing different hip devices include: 5,725,594; 5,702,485; 5,387,244; 5,376,124; 5,336,265; 5,330,536; 5,314,489; 5,314,479; 5,197,990; 5,167,666; 5,133,772; 5,116,377; 4,938,771; RE 32,488; 4,661,112; 4,642,124; 4,546,501; 4,514,865; 4,488,320; 4,406,023; and 4,359,785.

SUMMARY OF THE INVENTION

Novel prostheses and methods for their use, particularly in hip replacement, are provided. The subject prostheses are elongate devices having a proximal and distal end, where the devices have the following elements going from the proximal to distal end: (a) a ball component; (b) a neck component; (c) a curvilinear collar component; and (d) a stem component. Also provided are methods of implanting hip prostheses in a manner sufficient to provide for a pressure profile at the collar interface in which the pressure increases from the endosteal to the periosteal surface of the bone.

DESCRIPTION OF THE SPECIFIC EMBODIMENTS

Figure 1A:
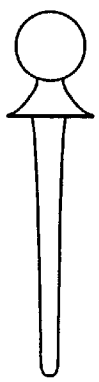
FIGS. 1A and 1B each provide a representation of a femoral prosthesis with a flat collar.
Figure 1B:
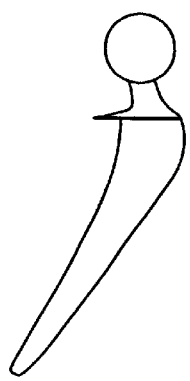
Figure 2A:
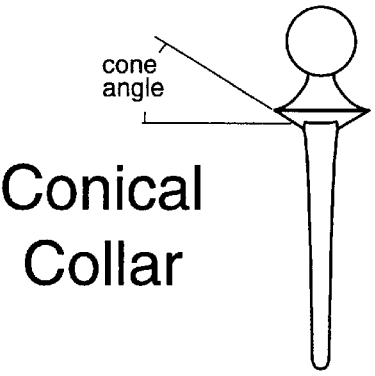
FIGS. 2A and 2B each provide a representation of a femoral prosthesis with a conical collar.
Figure 2B:
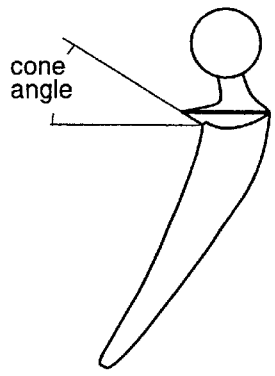
Figure 3A:
FIGS. 3A and 3B each provide a representation of a tapered femoral prosthesis.
Figure 3B:

Novel prostheses, particularly femoral prostheses, are provided. The subject prostheses are characterized by the presence of a curvilinear collar. Also provided are methods of implanting hip prostheses in a manner sufficient to provide for a pressure profile at the collar interface in which the pressure increases from the endosteal to the periosteal surface of the bone. In further describing the subject invention, the novel devices will be described first in greater detail, followed by a discussion of the novel methods of the invention in which the subject devices, as well as other femoral prostheses, may be implanted.

Before the subject invention is further described, it is to be understood that the invention is not limited to the particular embodiments of the invention described below, as variations of the particular embodiments may be made and still fall within the scope of the appended claims. It is also to be understood that the terminology employed is for the purpose of describing particular embodiments, and is not intended to be limiting. Instead, the scope of the present invention will be established by the appended claims.

In this specification and the appended claims, the singular forms "a," "an," and "the" include plural reference unless the context clearly dictates otherwise. Unless defined otherwise, all technical and scientific terms used herein have the same meaning as commonly understood to one of ordinary skill in the art to which this invention belongs.

In the broadest sense, the prostheses of the subject invention are devices designed for use in the replacement of joints having a ball and socket motif. As such, the subject devices are designed for use in the replacement of both hip and shoulder joints, i.e., they are femoral or shoulder (humeral) prostheses. The subject devices are particularly suited for use as femoral prostheses.

The subject devices comprise the following four distinct components going from the proximal to distal end: (a) a ball component; (b) a neck component; (c) a curvilinear collar component; and (d) a stem component. The ball or head component of the device may have any convenient configuration, including the same configuration as any one of the already known prostheses. Generally, the ball component will be at least hemispherical in shape, and may be closer to a full spherical shape. The dimensions of the ball component will vary depending on the joint in which the device is to be used and the particular host into which the device is to be implanted. For femoral prostheses for use in humans, the diameter of the head will vary depending on whether the prosthesis is a total prosthesis, in which the acetabulum is replaced, or a hemi-prosthesis, in which the acetabulum is not replaced. As such, the diameter of the head will be at least about 15 mm, usually at least about 20 mm and may be as large as 60 mm or larger, but will usually not exceed from about 50 to 55 mm. For total hip replacement prostheses, the diameter of the head will typically range from about 15 to 35 mm, usually from about 20 to 35 mm, while for hemi-prostheses, the diameter of the head will typically range from about 45 to 65 mm, usually from about 50 to 60 mm, and more usually from about 50 to 55 mm.

The neck component of the device extends from the base of the ball component and to the collar component, described in greater detail below. The neck component will generally be about 10 mm, usually at least about 15 mm in length, and may be as long as 55 mm or longer, but will usually not exceed about 50 mm in length. The neck component may have a variety of cross-sectional shapes and configurations, where representative cross-sectional shapes include circular, elliptical, square, trapezoidal, or irregular, where the neck may or may not be tapered or flared or stepped, and may or may not have the same cross-sectional shape along its entire length.

The next component is a critical component of the subject devices and is the collar. The collar of the device may extend around the entire circumference of the device, or just a portion thereof, e.g., the collar may extend around 90% of the circumference of the device, 50% of the circumference of the device, or less. Generally, the collar will at least be present on the medial surface of the device. The collar is curvilinear, by which is meant that at least one lower cross-sectional profile of the collar has a two-dimensional curvilinear shape. The lower cross-sectional profile of the collar is the lower periphery of any cross-sectional view of the collar, where the cross-sectional view is provided by a plane passing through the collar along the Z axis of the collar, where the Z axis is perpendicular to the X-Y plane, which is occupied by the outer edge of the collar. The curvilinear profile may be arcuate or inverse arcuate, elliptical or inverse elliptical, or some other curvilinear shape. Generally, the curvilinear shape will be free of inflection points.

Figure 4A:
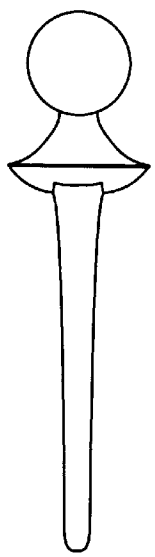
FIGS. 4A through 4D provide representations of different femoral prostheses having a curvilinear collar according to the subject invention.
Figure 4B:
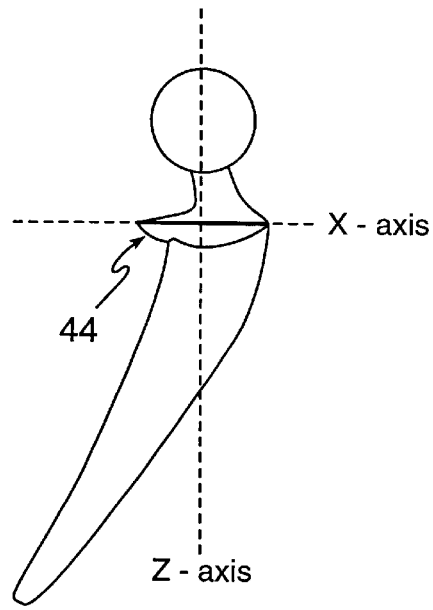

FIGS. 4A through 4D provide elevation views of the two representative devices of the subject invention having curvilinear collars. In FIGS. 4A and 4B, the lower cross-sectional profile 44 is arcuate while in FIGS. 4C and 4D the lower cross-sectional profile is inverse arcuate.

In the curvilinear collars of the subject devices, the entire collar need not have a curvilinear lower cross-sectional profile. In other words, a portion of the collar may have a lower cross-sectional profile that is linear or some other non-curvilinear shape. In many embodiments, however, the lower cross-sectional profile at any point on the collar will be curvilinear.

Figure 4C:
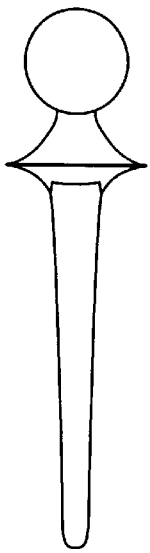
Figure 4D:
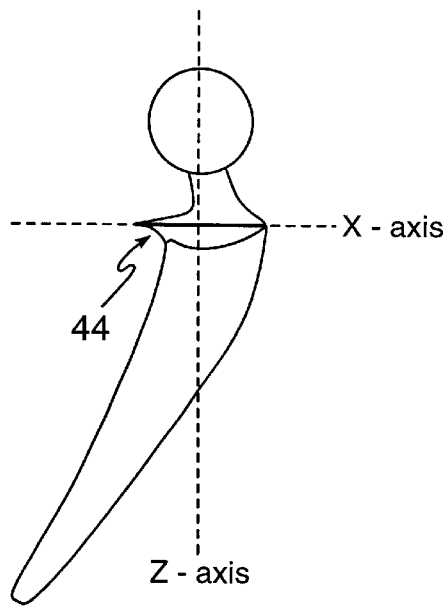

In a preferred embodiment, the lower cross-sectional profile has an inverse curvilinear, e.g., inverse arcuate, shape, such as the device shown in FIGS. 4C and 4D. In this preferred embodiment, the particular inverse curvilinear shape provides for a pressure profile at the collar interface between the implant and bone (under loads that include a compressive component) in which the pressure increases from the inner (endosteal) to the outer (periosteal) surface of the bone. The resulting stresses and strains in the bone in the region of the implant collar produce a strain energy density pattern that approximates the strain energy density pattern in comparable bone under normal physiological conditions, i.e., in a control environment such as normal healthy bone, under bending, oblique, or torsional external loads. By "approximates" is meant that the bone strain energy density increases from the endosteal to the periosteal surface of the bone, as occurs in normal bone under bending, oblique, or torsional external loads, which is the reverse of the strain energy density pattern produced by conical and tapered prostheses in which the mating collar and bone surfaces are of matching shape. The degree of approximation is controlled by the specific dimensions of the inverse curvilinear lower cross-sectional profile of the prosthesis collar. In any event, in order to provide for enhanced bone maintenance and increased implant longevity as compared to what is experienced with present collar designs, the specific collar dimensions should be such as to provide for at least one of: (a) more physiological strain energy density distribution in the bone in the region of the implant collar, or (b) a more optimal interface stress distribution.

Joined to the collar and extending to the distal end of the device is the distinct stem component. The stem component may be any convenient form and may be similar or identical to any of the number of different stem designs currently known to those of skill in the art. As such, the stem may be relatively linear, curved or bent, have a variety of shapes and configurations, be tapered or flared, etc. The particular stem configuration will be chosen as a matter of convenience in view of the particular application in which it is to be employed. Generally, the stem component will be at least about 75 mm, usually at least about 80 mm and more usually at least about 90 mm in length, where the stem component may be as long as 350 mm or longer, but will usually not exceed about 300 mm in length.

Importantly, the subject devices comprise distinct collar and stem components, such that these two components are not configured so as to be indistinguishable from each other, i.e., the collar does not extend down the device for the entire length of the stem to the point most distal from the ball of the device.

The various components may be fabricated from a variety of different materials, as is known in the art, where generally the material will be biocompatible. Materials from which the device may be fabricated include medical grade alloys, such as cobalt-chromium alloy, titanium alloy, stainless steel; ceramics; composite materials, and the like. The device may be fabricated entirely from the same material, or different components of the device fabricated from different materials. One or more surfaces of the device may be modified as convenient to impart desired properties to the device, such as made porous, coated with hydroxyapatite layer, and the like.

The devices may be fabricated using any convenient methodology, where the particular methodology employed will be chosen as a matter of convenience and/or economy. As such, the devices may be machined, molded and the like.

The devices may be used in accordance with methods already developed by those of skill in the art for implanting other prostheses. Generally, the region of the implant will be prepared, which preparation will generally include removal of compromised bone, such as portions of the femur, reaming of the bone, such as the intramedullary canal, etc. If a bone cement is to be employed, it will be introduced into the void space of the prepared bone. The implant will then be introduced into the bone.

In a preferred method, the subject device is implanted in a manner to provide for a pressure profile at the collar interface between the implant and bone, under loads that include a compressive component, in which the pressure increases from the inner (endosteal) to the outer (periosteal) surface of the bone. One means of achieving such a pressure profile is to implant the device into a bone that has been prepared such that the mating surface between the collar and the bone is mismatched in shape. The mismatch between the mating bone surface and the collar will be sufficient to result in the bone in the region of the implant collar being subjected to stresses that produce a strain energy density pattern that approximates the strain energy density pattern in comparable bone under normal physiological conditions, i.e., in a control environment such as normal healthy bone, under bending, oblique, or torsional external loads. By "approximates" is meant that the bone strain energy density increases from the endosteal to the periosteal surface of the bone, as occurs in normal bone under bending, oblique, or torsional external loads, which is the reverse of the strain energy density pattern produced by conical and tapered prostheses in which the mating collar and bone surfaces are of matching shape. The degree of approximation is controlled by the shape of the prosthesis collar and the details of the mismatch between the mating collar and bone surfaces. One way to achieve the above results is to intentionally mismatch the mating bone surface and the collar in a manner such that the implant first contacts the bone near the periosteal bone surface. In any event, in order to provide for enhanced bone maintenance and increased implant longevity as compared to what is experienced with present methods in which the collar and bone interface surfaces are substantially matched in shape, the intentional mismatch should be such as to provide for at least one of: (a) a more physiological strain energy density distribution in the bone in the region of the implant collar, or (b) a more optimal interface stress distribution.

While the above preferred method has been described in terms of use of the devices of the subject invention having curvilinear collars, it is not limited to use with such implants. As such, the above methods in which one intentionally mismatches the collar with the mating bone interface may be used with other prostheses. Representative prostheses in which the above mismatch method may be used include: cemented prostheses, such as the Charnley-style prostheses, the T-28, the TR-28, the Modell St. George, the Mark I, the Mark II, the Freeman femoral neck prosthesis, other stainless steel and titanium alloy prostheses, and the like; cementless prostheses, such as the Anatomic Medullary Locking (AML) prosthesis, the Porous Coated Anatomic (PCA) prosthesis, the Tri-Lock femoral system, the Mallory Head system, the McKee-Farrar prosthesis and the like, as well as those devices described in U.S. Pat. Nos. 5,702,485; 5,387,244; 5,376,124; 5,336,265; 5,330,536; 5,314,489; 5,314,479; 5,197,990; 5,167,666; 5,133,772; 5,116,377; 4,938,771; RE 32,488; 4,661,112; 4,642,124; 4,546,501; 4,514,865; 4,488,320; 4,406,023; and 4,359,785, the disclosures of which are herein incorporated by reference.

Also provided are kits comprising the subject curvilinear prostheses. The subject kits will at least include a prosthesis having a curvilinear collar, as described above. In addition, the kits will generally include instructional material on how to use the subject devices, where such instructional material could be present on a package insert and/or associated with the device or package labeling, where the instructional material will preferably include details on how to implant the device in a manner sufficient to achieve a physiological distribution of pressure between the implant and the bone. The kits may further comprise an acetabular cup component designed to be used with the device. A variety of acetabular cups have been developed which can be included in the subject kits, where such cups include those described in U.S. Pat. Nos. 5,571,111; 5,549,697; 5,405,403; 5,370,704; 5,290,315; 5,192,329; 5,127,920; 4,892,551; 4,878,918; 4,141,088, the disclosures of which are herein incorporated by reference. The kits may also include a bone cement for cementing the device in the bone. A variety of bone cements have been developed and are suitable for inclusion in the subject kits, where representative cements include polymeric compositions, such as polymethyl methacrylate, calcium phosphate cements, and the like.

The prostheses and methods for their implantation can be used with a variety of different hosts, where suitable hosts are generally mammalian, such as rare or exotic animals, e.g., zoo animals, pets; domestic animals, e.g., livestock and pets; and the like, where the subject devices are particularly suited for use with humans.

It is evident from the above results and discussion that improved prostheses, particularly femoral prostheses, are provided. In many situations, the subject devices offer advantages in terms of outcome over earlier device designs. Importantly, the subject devices having a curvilinear collar result in the maintenance of mechanical stimulus (strain energy density, SED, stored within the bone) at the proximal (upper) end of the femur, which further results in reduced deleterious shear stresses at the implant/bone interface providing for improved short and long term outcomes. Furthermore, the subject methods of implanting femoral prostheses yield improved long term results, as the bone at the implant interface is subjected to stresses which are analogous (though not necessarily identical) to those experienced by bone under normal physiological conditions, providing for improved outcomes as compared to situations where conventional implant methodology is employed, i.e., where the implant and bone are matched in shape.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. A prosthesis comprising from a proximal to distal end:

a ball;

a neck;

a collar, wherein said collar has a lower cross-sectional profile that is inverse curvilinear as shown in FIGS. 4C and 4D; and a stem.

2. The prosthesis according to claim 1, wherein said prosthesis is dimensioned for use as a femoral prosthesis.

3. The prosthesis according to claim 1, wherein said prosthesis is dimensioned for use as a humeral prosthesis.

4. A femoral prosthesis comprising from a proximal to distal end:

a ball;

a neck;

a collar, wherein said collar has a lower cross-sectional profile that is inverse curvilinear as shown in FIGS. 4C and 4D; and a stem.

5. In a femoral prosthesis, the improvement comprising:

a curvilinear collar having a lower cross-sectional profile that is inverse curvilinear as shown in FIGS. 4C and 4D.

6. A kit for use in total hip arthroplasty, said kit comprising:

a femoral prosthesis comprising:

a ball;

a neck;

a collar, wherein said collar has a lower cross-sectional profile that is inverse curvilinear as shown in FIGS. 4C and 4D; and a stem.

7. The kit according to claim 6, further comprising an acetabular cup.

8. The kit according to claim 6, further comprising a bone cement.

* * * * *